US008343524B2

(12) United States Patent
Willis et al.

(10) Patent No.: US 8,343,524 B2
(45) Date of Patent: Jan. 1, 2013

(54) EXTENDED RELEASE TABLET AND METHOD FOR MAKING AND USING SAME

(75) Inventors: Michael Dean Willis, Elgin, IL (US); Marie Elizabeth Saunders, Schaumburg, IL (US)

(73) Assignee: Clarke Mosquito Control Products, Inc., Roselle, IL (US)

( * ) Notice: Subject to any disclaimer, the term of this patent is extended or adjusted under 35 U.S.C. 154(b) by 458 days.

(21) Appl. No.: 12/533,937

(22) Filed: Jul. 31, 2009

(65) Prior Publication Data

US 2010/0029486 A1    Feb. 4, 2010

Related U.S. Application Data

(60) Provisional application No. 61/093,054, filed on Aug. 29, 2008, provisional application No. 61/085,315, filed on Jul. 31, 2008.

(51) Int. Cl.
| | | |
|---|---|---|
| *A01N 25/34* | (2006.01) | |
| *A61K 9/20* | (2006.01) | |
| *A61K 9/46* | (2006.01) | |
| *A61K 9/22* | (2006.01) | |
| *A61K 9/26* | (2006.01) | |
| *A61K 9/24* | (2006.01) | |

(52) U.S. Cl. ........ 424/408; 424/464; 424/465; 424/466; 424/468; 424/469; 424/472

(58) Field of Classification Search .................. None
See application file for complete search history.

(56) References Cited

U.S. PATENT DOCUMENTS

| | | |
|---|---|---|
| 3,274,052 A | 9/1966 | Yaffe et al. |
| 3,687,386 A | 8/1972 | Sandbach |
| 3,732,206 A | 5/1973 | Kovats |
| 3,873,725 A | 3/1975 | Skinner et al. |
| 3,892,905 A | 7/1975 | Albert |
| 3,898,039 A | 8/1975 | Lin |
| 3,917,814 A | 11/1975 | Hedges et al. |
| 3,920,442 A | 11/1975 | Albert et al. |
| 4,041,151 A | 8/1977 | Milionis et al. |
| 4,331,652 A | 5/1982 | Ludwig et al. |
| 4,374,126 A | 2/1983 | Cardarelli et al. |
| 4,379,168 A | 4/1983 | Dotolo |
| 4,464,317 A | 8/1984 | Thies et al. |
| 4,584,319 A | 4/1986 | Lover et al. |
| 4,629,621 A | 12/1986 | Snipes |
| 4,631,857 A | 12/1986 | Kase et al. |
| 4,670,039 A | 6/1987 | Sjogren |
| 4,732,762 A | 3/1988 | Sjogren |
| 4,806,359 A | 2/1989 | Radebaugh et al. |
| 4,818,534 A | 4/1989 | Levy |
| 4,820,522 A | 4/1989 | Radebaugh et al. |
| 4,876,091 A | 10/1989 | Clarke, Jr. |
| 4,917,837 A | 4/1990 | Clarke, Jr. |
| 4,971,796 A | 11/1990 | Sjogren |
| 4,983,389 A | 1/1991 | Levy |
| 4,983,390 A | 1/1991 | Levy |
| 4,985,251 A | 1/1991 | Levy |
| 4,997,642 A | 3/1991 | Curtis et al. |
| 5,004,613 A | 4/1991 | Radebaugh et al. |
| 5,051,261 A | 9/1991 | McGinity et al. |
| 5,073,380 A | 12/1991 | Babu et al. |
| 5,160,530 A | 11/1992 | Misselbrook et al. |
| 5,169,645 A | 12/1992 | Shukla et al. |
| 5,180,585 A | 1/1993 | Jacobson et al. |
| 5,200,193 A | 4/1993 | Radebaugh et al. |
| 5,279,832 A | 1/1994 | Greissinger et al. |
| 5,302,223 A | 4/1994 | Hale |
| 5,338,533 A | 8/1994 | Derrieu |
| 5,371,109 A | 12/1994 | Engstrom et al. |
| 5,407,687 A | 4/1995 | Coffin et al. |
| 5,412,005 A | 5/1995 | Bastioli et al. |
| 5,439,683 A | 8/1995 | Hodakowski |
| 5,487,614 A | 1/1996 | Hale |
| 5,488,907 A | 2/1996 | Xu et al. |
| 5,567,430 A | 10/1996 | Levy |
| 5,569,639 A | 10/1996 | Beestman |
| 5,601,023 A | 2/1997 | Hale et al. |

(Continued)

FOREIGN PATENT DOCUMENTS

| | | |
|---|---|---|
| EP | 0453397 | 10/1991 |
| EP | 0624366 | 11/1994 |
| EP | 0631781 | 1/1995 |
| EP | 0647448 | 4/1995 |
| EP | 1882414 | 1/2008 |
| FR | 2156333 | 5/1973 |
| GB | 931160 | 7/1963 |
| GB | 1435678 | 5/1976 |
| GB | 2111830 | 7/1983 |
| JP | 5271014 | 10/1993 |
| WO | 90/04386 | 5/1990 |
| WO | 92/20229 | 11/1992 |
| WO | 93/01804 | 2/1993 |
| WO | 96/28973 | 9/1996 |
| WO | WO-96/28973 | * 9/1996 |
| WO | 00/25743 | 5/2000 |
| WO | 00/25757 | 5/2000 |
| WO | 2007/034250 | 3/2007 |
| WO | 2008/008592 | 1/2008 |

OTHER PUBLICATIONS

International Search Report and Written Opinion for Application No. PCT/US2009/052486 dated Jul. 26, 2010 (12 pages).

*Primary Examiner* — Alton Pryor

(74) *Attorney, Agent, or Firm* — Michael Best & Friedrich LLP

(57) ABSTRACT

Provided are cap layer compositions and base layer compositions, providing quick and extended release of an active ingredient, respectively, when placed in water. Further provided are dual release compositions including a base composition and a cap composition. The base composition may include a plaster and an active agent, and it may further include at least one of a water-soluble binder, a non-water-soluble binder, and a lubricant. The cap composition may include a plaster and an active agent, and it may further include at least one of a disintegrating agent, a non-water-soluble binder, and a lubricant. The compositions may be heated and mixed and formed into a tablet. Further provided are methods of making the compositions. Further provided are methods of controlling or eliminating pests and methods of increasing the potability of water. The compositions are effective for controlling or eliminating pests such as mosquitoes when applied at an application site.

24 Claims, No Drawings

U.S. PATENT DOCUMENTS

| | | |
|---|---|---|
| 5,610,214 A | 3/1997 | Olson |
| 5,635,194 A | 6/1997 | Dorn et al. |
| 5,640,180 A | 6/1997 | Hale et al. |
| 5,642,141 A | 6/1997 | Hale et al. |
| 5,643,591 A | 7/1997 | Mehra et al. |
| 5,645,843 A | 7/1997 | Cannelongo |
| 5,679,364 A | 10/1997 | Levy |
| 5,698,210 A | 12/1997 | Levy |
| 5,707,534 A | 1/1998 | Del Corral et al. |
| 5,720,329 A | 2/1998 | Clarke, Jr. |
| 5,720,967 A | 2/1998 | Hall-Hibbitts et al. |
| 5,734,396 A | 3/1998 | Hale et al. |
| 5,767,253 A | 6/1998 | Turner et al. |
| 5,785,976 A | 7/1998 | Westesen et al. |
| 5,815,980 A | 10/1998 | Clarke, Jr. |
| 5,824,328 A | 10/1998 | Levy |
| 5,830,263 A | 11/1998 | Hale et al. |
| 5,846,553 A | 12/1998 | Levy |
| 5,849,240 A | 12/1998 | Miller et al. |
| 5,858,384 A | 1/1999 | Levy |
| 5,858,386 A | 1/1999 | Levy |
| 5,858,406 A | 1/1999 | Stead et al. |
| 5,885,602 A | 3/1999 | Levy |
| 5,885,605 A | 3/1999 | Levy |
| 5,897,877 A | 4/1999 | Birrenbach et al. |
| 5,902,596 A | 5/1999 | Levy |
| 5,939,086 A | 8/1999 | Levy |
| 5,961,843 A | 10/1999 | Hayakawa et al. |
| 5,985,843 A | 11/1999 | Higo et al. |
| 6,001,382 A | 12/1999 | Levy |
| 6,015,773 A | 1/2000 | Wysong et al. |
| 6,113,935 A | 9/2000 | Rodson et al. |
| 6,146,652 A | 11/2000 | Gore et al. |
| 6,335,027 B1 | 1/2002 | Levy |
| 6,337,078 B1 | 1/2002 | Levy |
| 6,337,079 B1 | 1/2002 | Maindron |
| 6,346,262 B1 | 2/2002 | Levy |
| 6,350,461 B1 | 2/2002 | Levy |
| 6,355,675 B1 | 3/2002 | Beestman et al. |
| 6,387,386 B1 | 5/2002 | Levy |
| 6,389,740 B2 | 5/2002 | Perich et al. |
| 6,391,262 B1 | 5/2002 | Brinton et al. |
| 6,391,328 B1 | 5/2002 | Levy |
| 6,391,336 B1 | 5/2002 | Royer |
| 6,410,054 B1 | 6/2002 | Thosar et al. |
| 6,425,331 B1 | 7/2002 | Xu et al. |
| 6,437,000 B1 | 8/2002 | Mulye |
| 6,439,710 B1 | 8/2002 | Hale et al. |
| RE37,890 E | 10/2002 | Levy |
| 6,486,249 B1 | 11/2002 | Dituro et al. |
| 6,488,370 B2 | 12/2002 | Hale et al. |
| 6,512,012 B1 | 1/2003 | Levy |
| 6,524,618 B1 | 2/2003 | Kumar et al. |
| 6,534,093 B1 | 3/2003 | Thosar et al. |
| 6,558,707 B1 | 5/2003 | Thosar et al. |
| 6,572,872 B2 | 6/2003 | Voris et al. |
| 6,593,299 B1 | 7/2003 | Bennett et al. |
| 6,605,302 B2 | 8/2003 | Faour et al. |
| 6,610,326 B2 | 8/2003 | Chen et al. |
| 6,624,242 B2 | 9/2003 | Curry et al. |
| 6,630,486 B1 | 10/2003 | Royer |
| 6,645,524 B2 | 11/2003 | Midha et al. |
| 6,662,491 B2 | 12/2003 | Flinn et al. |
| 6,667,277 B2 | 12/2003 | Hartmann et al. |
| 6,670,311 B1 | 12/2003 | Aldcroft et al. |
| 6,682,759 B2 | 1/2004 | Lim et al. |
| 6,686,317 B2 | 2/2004 | Netherland et al. |
| 6,693,131 B2 | 2/2004 | Noeding et al. |
| 6,703,350 B2 | 3/2004 | Fujita et al. |
| 6,743,439 B1 | 6/2004 | Castillo et al. |
| 6,776,996 B2 | 8/2004 | Sun et al. |
| 6,780,424 B2 | 8/2004 | Claude |
| 6,803,051 B1 | 10/2004 | Voris et al. |
| 6,827,750 B2 | 12/2004 | Drozd et al. |
| 6,827,874 B2 | 12/2004 | Souter et al. |
| 6,835,218 B1 | 12/2004 | Drozd et al. |
| 6,852,328 B1 | 2/2005 | Voris et al. |
| 6,858,142 B2 | 2/2005 | Towndrow |
| 6,858,634 B2 | 2/2005 | Asrar et al. |
| 6,860,241 B2 | 3/2005 | Martin et al. |
| 6,861,389 B2 | 3/2005 | Giencke et al. |
| 6,878,309 B2 | 4/2005 | Blakemore et al. |
| 6,884,878 B2 | 4/2005 | Borovsky et al. |
| 6,905,707 B2 | 6/2005 | Byrd |
| 6,927,240 B2 | 8/2005 | Schmid et al. |
| 6,998,132 B1 | 2/2006 | Ueda et al. |
| 7,001,534 B2 | 2/2006 | Landis et al. |
| 7,018,643 B2 | 3/2006 | Puterka et al. |
| 7,063,804 B2 | 6/2006 | Landis et al. |
| 7,067,153 B2 | 6/2006 | Grisoni |
| 7,163,687 B1 | 1/2007 | Murphy et al. |
| 7,196,116 B1 | 3/2007 | Wilkins et al. |
| 7,220,434 B2 | 5/2007 | Desai et al. |
| 7,263,845 B2 | 9/2007 | Lee |
| 7,294,343 B2 | 11/2007 | Barresi et al. |
| 7,296,378 B1 | 11/2007 | Cobb et al. |
| 7,335,374 B2 | 2/2008 | Voris et al. |
| 7,348,019 B1 | 3/2008 | Murphy et al. |
| 7,364,748 B2 | 4/2008 | Claude |
| 7,399,324 B2 | 7/2008 | Roddenbery et al. |
| 7,524,434 B2 | 4/2009 | Blakemore et al. |
| 2001/0001658 A1 | 5/2001 | Chen et al. |
| 2003/0099710 A1 | 5/2003 | Chen et al. |
| 2003/0215508 A1 | 11/2003 | Davis et al. |
| 2004/0018233 A1 | 1/2004 | Davis et al. |
| 2004/0022851 A1 | 2/2004 | Davis et al. |
| 2004/0202761 A1 | 10/2004 | Kochhar et al. |
| 2004/0228918 A1 | 11/2004 | Chen et al. |
| 2004/0253311 A1 | 12/2004 | Berlin et al. |
| 2005/0249792 A1 | 11/2005 | Kugelmann |
| 2006/0013875 A1 | 1/2006 | Han et al. |
| 2006/0099257 A1 | 5/2006 | Langridge et al. |
| 2006/0134207 A1 | 6/2006 | Srinivasan et al. |
| 2006/0141037 A1 | 6/2006 | Mehta et al. |
| 2006/0239977 A1 | 10/2006 | Sjogren et al. |
| 2007/0140957 A1* | 6/2007 | Mohanty et al. ............ 424/1.11 |
| 2007/0184983 A1 | 8/2007 | Finch et al. |
| 2007/0281020 A1 | 12/2007 | Ulloa et al. |
| 2008/0057122 A1 | 3/2008 | Toney-Parker et al. |

* cited by examiner

EXTENDED RELEASE TABLET AND METHOD FOR MAKING AND USING SAME

CROSS-REFERENCE TO RELATED APPLICATIONS

This application claims priority to U.S. Provisional Application No. 61/085,315 filed Jul. 31, 2008, and U.S. Provisional Application No. 61/093,054 filed Aug. 29, 2008, both of which are incorporated herein by reference in their entirety.

FIELD OF USE

This invention relates to extended release tablets, and particularly, their use in pest control applications. It also relates to dual release tablets containing active ingredient in an immediate release matrix and active ingredient in an extended release matrix. The invention also relates to methods of making dual release and extended release tablets.

BACKGROUND

Over the years, considerable effort has been expended to control pest (e.g., mosquito) populations. Pest control tablets that can provide an extended release of a pest control composition are desirable.

SUMMARY

In one aspect the invention provides a method for forming a composition comprising mixing without adding water at least one active agent, a plaster, and a binder, wherein the composition provides an extended release of the active agent over a period of at least 30 days when placed in water.

In another aspect, the invention provides a method for forming a composition comprising mixing without adding water at least one active agent, a plaster, and a binder, wherein the composition provides a quick release of the active agent over a period of less than 10 minutes when placed in water.

In another aspect, the invention provides a dual-release composition comprising a cap composition comprising at least one active agent and a plaster, and a base composition comprising at least one active agent and a plaster. The cap composition may provide a quick release of the active agent over a period of less than 10 minutes, and the base composition may provide an extended release of the active agent over a period of at least 30 days when placed in water.

In another aspect, the invention provides a tablet comprising a plaster and at least one active agent selected from the group consisting of a pesticide, insecticide, herbicide, fungicide, nematicide, acaricide, bactericide, rodenticide, miticide, algicide, germicide, repellant, and nutrient.

In another aspect, the invention provides a method of making an extended release solid matrix, wherein the method comprises mixing at least one active agent, a plaster, and a binder to form a mixture, heating the mixture at about 40° C. to about 75° C., and cooling the mixture. The method may further comprise breaking up the cooled mixture into granules and compressing the granules into a tablet.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

It also is understood that any numerical range recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this application.

In one aspect, the invention may provide a composition comprising at least one of a cap composition and a base composition. The cap composition may comprise at least one of an active ingredient, a disintegrating agent, a plaster, a water-soluble binder, a non-water soluble binder, a lubricant, and combinations thereof. The base composition may comprise at least one of an active ingredient, a plaster, a water-soluble binder, a non-water soluble binder, a lubricant, and combinations thereof. The cap composition may provide a quick release of the active ingredient and the base composition may provide an extended release of the active ingredient. The cap composition and the base composition may be in tablet form.

In another aspect, the invention may provide a composition comprising at least one of an active ingredient, a plaster, a water-soluble binder, a non-water soluble binder, a lubricant, and combinations thereof. The composition may provide an extended release of the active ingredient over a period of time. The composition may be in tablet form.

In another aspect, the invention may provide a composition comprising at least one of an active ingredient, a plaster of Paris, a polyethylene glycol, a non-water soluble binder, a lubricant, and combinations thereof. The composition may provide an extended release of the active ingredient over a period of time. The composition may be in tablet form.

In a further aspect, the invention may provide a composition comprising at least one of an active ingredient, a disintegrating agent or disintegrant, a plaster, a water-soluble binder, non-water soluble binder, and combinations thereof. The composition may further comprise a lubricant. The composition may provide a quick release of the active ingredient. The composition may be in tablet form.

In yet another aspect, the invention may provide a method of making a composition that comprises blending an active ingredient, a plaster, a water-soluble binder, and a non-water soluble binder to form a mixture. The mixture may be heated to about 40° C. to about 75° C. until the mixture granulates to form granules. The mixture may also be mixed during heating. In another aspect, the mixture may be heated until about 60° C. to about 65° C. until the mixture granulates. In another aspect, the mixture may be heated to about 40° C. to about 75° C. and form a pliable mass. The pliable mass may be forced through an extruder and cooled, and the extrudates may be broken into granules. The pliable mass may be cooled and become hard, and the hard mass may be broken into granules. The granules may also be screened for a particle size from about −20 mesh to about +60 mesh and then compressed into a tablet.

In another aspect, the invention may provide a composition comprising at least one of an active ingredient, a water-soluble binder, and a plaster. The active ingredient, the water-soluble binder, and the plaster may form a matrix. The matrix may provide extended release of the active ingredient over a period of time. The composition may also comprise a non-water soluble binder. The non-water soluble binder may act to slow down the rate the matrix dissolves. The composition may be in tablet form.

In yet another aspect, the invention may provide a composition comprising at least one of an active ingredient, a polyethylene glycol, and a plaster of Paris. The active ingredient, the polyethylene glycol, and the plaster of Paris may form a matrix. When the composition is placed in water, the polyethylene glycol may dissolve and the plaster of Paris may hydrolyze into gypsum, forming a gypsum matrix that incorporates the active ingredient. The gypsum matrix may hold its shape and provide an extended release of the active ingredient over a period of time. The composition may also comprise a non-water soluble binder. The non-water soluble binder may act to slow down the rate the matrix dissolves. The composition may be in tablet form.

In one embodiment, the invention may provide a dual release composition comprising a cap composition or top layer and a base composition or bottom layer. The cap composition and base composition may have different release rate characteristics. The dual release composition may be in tablet form.

The cap composition may comprise a quick release matrix which may comprise at least one of an active ingredient, a disintegrating agent, a plaster, a non-water soluble binder, a water-soluble binder, a lubricant, and combinations thereof. The composition may provide a quick release of active ingredient and subsequent initial control. The base composition may comprise an extended release matrix which may comprise at least one of an active ingredient, a plaster, a water soluble binder, a non-water soluble binder, a lubricant and combinations thereof. The base composition may provide extended release of active ingredient over a period of time.

In another embodiment, the invention may provide an extended release composition comprising an active ingredient, a plaster, a water soluble binder, a non-water soluble binder, a lubricant and combinations thereof. This tablet may provide an extended release over a period of time. The extended release composition may be in tablet form.

In a further embodiment, the invention may provide a quick release composition comprising at least one of an active ingredient, a disintegrating agent, a plaster, a non-water soluble binder, water-soluble binder, a lubricant, and combinations thereof. The composition may provide a quick release of active ingredient. The quick release composition may be in tablet form.

As used herein, the term "quick release" means that the release of active ingredient from the tablet when the tablet is placed in water may occur over periods of less than about 10 minutes, particularly less than about 5 minutes, and more particularly less than about 3 minutes. Suitably, the release of the active agent is complete within about 10 minutes, particularly within about 5 minutes, and more particularly within about 3 minutes.

As used herein, the term "extended release composition" or "extended release" means that the release of active ingredient from the tablet when the tablet is placed in water may occur over periods of at least about 30 days, at least about 60 days, at least about 90 days, or at least about 150 days. If the extended release composition is in tablet form, the tablet may be hard enough to slowly release active ingredient over a period of time.

Active ingredients may include, but are not limited to, pesticides, insecticides, herbicides, fungicides, nematicides, acaricides, bactericides, rodenticides, miticides, algicides, germicides, repellents, nutrients, and combinations thereof. Specific examples of insecticides include, but are not limited to, a botanical, a carbamate, a microbial, a dithiocarbamate, an imidazolinone, an organophosphate, an organochlorine, a benzoylurea, an oxadiazine, a spinosyn, a triazine, a carboxamide, a tetronic acid derivative, a triazolinone, a neonicotinoid, a pyrethroid, a pyrethrin, and a combination thereof. Specific examples of herbicides include, without limitation, a urea, a sulfonyl urea, a phenylurea, a pyrazole, a dinitroaniline, a benzoic acid, an amide, a diphenylether, an imidazole, an aminotriazole, a pyridazine, an amide, a sulfonamide, a uracil, a benzothiadiazinone, a phenol, and a combination thereof. Specific examples of fungicides include, without limitation, a dithiocarbamate, a phenylamide, a benzimidazole, a substituted benzene, a strobilurin, a carboxamide, a hydroxypyrimidine, a anilopyrimidine, a phenylpyrrole, a sterol demethylation inhibitor, a triazole, and a combination thereof Specific examples of acaricides or miticides include, without limitation, rosemary oil, thymol, spirodiclogen, cyflumetofen, pyridaben, diafenthiuron, etoxazole, spirodiclofen, acequinocyl, bifenazate, and a combination thereof. The tablets according to the invention may comprise an effective amount of the active agent. As used herein, "effective amount" means a quantity of a compound sufficient enough to provide a significant modification at an application site, for example, significant elimination of pests.

Plasters may include, but are not limited to, plaster of Paris, lime plaster, cement plaster, and combinations thereof. Specific examples of plasters include, without limitation, Terra Alba, Snow White Filler, Puritan Pottery Plaster, No. 1 Moulding Plaster, No. 2 Moulding Plaster, Duramold Pottery Plaster, C-Base Plaster, Hydrocal A-11, Hydrocal B-11, Hydrocal X-21 MC, No. 1 Casting Plaster, Dental Plaster, Casting Plaster, Potting Plaster, Ultracal 30 Gypsum Cement, Ultracal 60 Gypsum Cement (all available from United States Gypsum), and combinations thereof.

Water-soluble binders may include, without limitation, acaia, gelatin, tragacanth, sucrose, guar gum, bentonite, methylcellulose, carboxymethylcellulose, microcrystalline cellulose, polyvinylpyrrolidone, polyvinyl alcohol, polyacrylic acid, polyethylene glycols of varying molecular weights, salts of alginic acid, lignins, and combinations thereof. Specific examples of polyethylene glycols include polyethylene glycols with molecular weights in the range from about 1000 to about 8500, which include Carbowax 3350, Carbowax 4000, Carbowax 6000, Carbowax 8000, and combinations thereof.

Non-water soluble binders may include, without limitation, corn starch, pregelatinized starch, alginate, ethylcellulose, hydroxypropylcellulose, hydroxypropylmethylcellulose, polymethacrylate, dicalcium phosphate dihydrate, glyceryl behapate, and combinations thereof.

Disintegrants may include, without limitation, starch (corn, potato, wheat), pregelatinized starch, modified corn starch, sodium starch glycolate, citric acid, sodium bicarbonate, microcrystalline cellulose, gums (agar, guar, locust bean, pectin, tragacanth), croscarmellose sodium, alginic acid, resins, clays, surfactants, and combinations thereof. The disintegrant may be an effervescent.

Lubricants may include, without limitation, hydrogenated vegetable oils, mineral oil, talc, stearic acid, metallic stearates such as magnesium stearate, lauryl sulfate salts, boric acid, sodium chloride, sodium benzoate, sodium acetate, sodium oleate, polyethylene glycol, glyceryl behapate, and combinations thereof.

For the dual release composition, the amount of active ingredient in the base composition may be from about 0.01% to about 50% by weight, particularly about 0.1% to about 25% by weight, more particularly about 0.5% to about 12% by weight.

For the dual release composition, the amount of plaster in the base composition may be from about 40% to about 90% by weight, particularly about 50% to about 85% by weight, more particularly about 60% to about 85% by weight.

For the dual release composition, the amount of water-soluble binder in the base composition may be from about 5% to about 50% by weight, particularly about 5% to about 30% by weight, more particularly about 8% to about 20% by weight.

For the dual release composition, the amount of non-water soluble binder in the base composition may be from about 0% to about 30% by weight, particularly about 0% to about 20% by weight, more particularly about 0% to about 5% by weight.

For the dual release composition, the amount of lubricant added to the base composition post granulation may be from about 0% to about 1.5% by weight, particularly about 0.1% to about 1% by weight, more particularly about 0.4% to about 1% by weight.

For the dual release composition, the amount of active ingredient in the cap composition may be from about 0.01% to about 30% by weight, particularly about 0.1% to about 20% by weight, more particularly about 0.5% to about 10% by weight.

For the dual release composition, the amount of plaster in the cap composition may be from about 0% to about 40% by weight, particularly about 5% to about 30% by weight, more particularly about 10% to about 20% by weight.

For the dual release composition, the amount of disintegrate in the cap composition may be from about 20% to about 80% by weight, particularly about 35% to about 80% by weight, more particularly about 50% to about 75% by weight.

For the dual release composition, the amount of non-water soluble binder in the cap composition may be from about 2% to about 40% by weight, particularly about 5% to about 30% by weight, more particularly about 8% to about 15% by weight.

For the extended release composition, the amount of active ingredient may be from about 1.0% to about 50% by weight, particularly about 3% to about 30% by weight, more particularly about 5% to about 10% by weight.

For the extended release composition, the amount of plaster may be from about 40% to about 90% by weight, particularly about 50% to about 85% by weight, more particularly about 60% to about 85% by weight.

For the extended release composition, the amount of water-soluble binder may be from about 5% to about 50% by weight, particularly about 5% to about 30% by weight, more particularly about 8% to about 20% by weight.

For the extended release composition, the amount of lubricant added to the composition post granulation may be from about 0% to about 1.5% by weight, particularly about 0.1% to about 1% by weight, more particularly about 0.4% to about 1% by weight.

It was unexpectedly discovered that a controlled release composition comprising a binder (e.g. polyethylene glycol), a plaster (e.g., gypsum cement), an active agent, and optionally other solid excipients may be created without the use of water. The compositions and tablets of the present application may be prepared using different methods.

In one embodiment, the composition is prepared by first blending the ingredients described above to form a mixture. Suitably, the ingredients may be combined without adding water to the mixture. The mixture may be non-aqueous. The ingredients may be combined and mixed without the addition of water. When components of the invention are being mixed, "mixing without adding water" means the components are mixed while adding substantially no water. While some water may or may not inherently be present in the components being mixed, substantially no water is intentionally added. "Substantially no water" means no water or water in a nominal amount. A nominal amount is an amount insufficient to render a resulting mixture a wet blend. Mixing without adding water may comprise dry-blending the ingredients. The composition may be formed by dry-granulation. The mixture may be in a powder form. The ingredients may be blended in varying order (see the examples below).

In one embodiment, the mixture may be directly compressed into a tablet. To form tablets by direct compression, the ingredients may be combined without the addition of water to form a dry mixture that may be compressed without heating to form a tablet.

In another embodiment, the ingredients or mixture may be processed with heat. The ingredients may or may not be mixed before and/or during heating. Different equipment may be used for mixing and heating, including, but not limited to, blenders, paddle blenders, ribbon blenders, agitators, and extruders. The ingredients may be mixed and heated to from about 40° C. to about 75° C., particularly from about 50° C. to about 70° C., and more particularly from about 60° C. to about 65° C. The temperature may be adjusted depending on active ingredient temperature limits and the melting point of the ingredients.

Heat may be applied in a variety of ways. For example, the ingredients or mixture may be placed into a mixing container equipped with heating tapes around the outside of the container. Alternatively, the mixture may be placed in a rotating can and heat may be applied with a hand-held heat gun. Heating of the mixture provides an unexpected way to granulate the powders without the addition of water.

In one embodiment, with a combination of heat and intimate mixing using varying mixing cycles and times (see the examples below), the mixture may granulate without the addition of any liquids. The mixture may be heated and mixed until the mixture granulates to form individual granules. Heat and mechanical force may be applied to the mixture to form granules before the mixture is cooled. Suitably, the mixture may be heated to about 40° C. to about 70° C.

Granulation may involve the process of particle size enlargement where the mixture (in the form of a powder) is gathered together into larger, permanent aggregates whereby the aggregates become free-flowing. These granules may improve the flow of the mixture and enhance its compressibility.

In another embodiment, the mixture may be heated and form granules and continue to be heated past the granule stage to form a pliable solid mass or mixture and then forced under pressure through an orifice plate with specific diameter holes to form extrudates. The extrudates may cool quickly upon being extruded. The extrudates may be in the form of long, fine strands, which may be broken into granules. In one example the extrudates form about 0.7 mm diameter strands. Additionally, the diameter of the strand may be from about 0.6 mm to about 1.2 mm, depending on the selection of the diameter of the holes on the orifice plate.

In another embodiment, the mixture may be heated and form granules and continue to be heated past the granule stage to form a pliable solid mass or mixture. Upon cooling the pliable solid mass or mixture may become very hard. In order to use the mass, it may be broken up with force to form granules (for instance, a hammer can be used).

If the mixture forms granules or extrudates, portions can be milled through a Wiley mill, a hammer mill, a knife-type mill, or an oscillating mill. Milling may be used, but it may not be required. The granules or milled material from the pliable solid mass may be screened using a 10, 20, 30, 40, 50, and/or 60 mesh sieve. The desired particle size may then be selected to form a final granule mixture. The final granule mixture may be placed into a mixer. A lubricant may be added to coat the surface of the granules to prevent them from sticking to the die in the tablet press.

The different sieve fractions of granules may be compressed into a tablet. The 40 mesh sieve fraction may be used for a uniform-looking tablet. Alternatively, the 20, 30, 40, 50, and 60 mesh fractions can be combined in one sample that provides a uniform looking tablet with good flow properties. The particle size of the granules used for the dual release and extended release tablets may be in the range of −20+40 mesh, −16+60 mesh, −20+60 mesh, or −20+50 mesh. The particle size of the granules may be from about −8 mesh to about +150 mesh, particularly from about −10 mesh to about +80 mesh, and more particularly from about −20 mesh to about +60 mesh.

Compressed tablets may be prepared by the application of high pressure, using steel punches and dies to powders or granulations. The base composition may be compressed into a tablet to form an extended release tablet. In another embodiment, the cap composition may be compressed into a tablet to form a quick release tablet. In a further embodiment, the base and cap composition can be layered and compressed into a tablet to form a dual release tablet with a base composition layer and a cap composition layer. The base and the cap composition may be combined in any ratio. The ratio may be adjusted depending on the active ingredient. In yet another embodiment, the base composition and the cap composition may be combined and may contain different active ingredients.

The cap composition may be prepared by mixing the ingredients described above. The ingredients may be mixed in varying orders (see the examples below).

In one embodiment, an individual tablet is pressed by first pouring the base composition into a die of desired size and shape. The die may be tapped to level the ingredients and the composition may be pressed with the corresponding punch by hand to remove air to a uniform depth in the die. This process may be used for a dual release or extended release tablet. For a dual release tablet, the cap composition may be added to the tablet by pouring it into the die on top of the base composition. The die may be again tapped to level and then the punch may be placed on top of the cap and compressed using a hydraulic press. An Arbor press may be used to extract the tablet from the punch and die.

For commercial production, tablets may be prepared by a single station press or a multiple station or rotary tablet press. Examples of single station tablet presses include, without limitation, a Carver, Stokes, and Cadmach press. Examples of rotary tablet presses include, without limitation, a Fette Perfecta Press, a Colton Press, an Adept Engineers Press, a Stokes Press, a Manesty Beta Press, a Key International Press, a Korsch Press, and a Courtoy Press. Both the dual release and the extended release tablets may be pressed to about 5,000 to about 40,000 pounds, particularly to about 9,000 lbs to about 20,000 pounds, and more particularly about 10,000 to about 12,000 pounds. In one embodiment, small granules may be compressed under pressure using a punch and die assembly tablet press.

For commercial production of tablets, a mixture comprising a plaster and a binder may be heated to form a solid without the use of water. With heating, the glass transition temperature may be reached whereby the binder may be in a pliable, soft, flexible, rubbery state (plasticized) and the plaster may impart hardness to the mixture. For commercial production, an Extrud-O-Mix mixer/extruder (for example, model EM-6 with 15 hp motor; manufactured by Bepex International LLC, Minneapolis, Minn.) may be used. The mixer/extruder may be equipped with a jacket for heating and/or cooling in the mixing zone to plasticize the mixture by imparting heat and mechanical force. The end of the mixer/extruder may be mounted with an orifice plate with small holes (for example, about 0.5 mm to 3.0 cm, suitably about 0.5 mm to 1.5 mm diameter holes) through which the plasticized composition may be extruded to form long strands. The strands may be immediately cooled and fed to an oscillating granulator. An oscillating granulator may break up the strands into smaller pieces. The smaller pieces or granules may be fed to a separator (for example, a Sweco separator) to select for a particular granule size (for example, −20+60 mesh).

The compositions of the present invention may be compressed into a hard, dust-free tablet having an aesthetically pleasing waxy appearance. The base composition of the dual release tablet and the extended release tablet may have a waxy-looking appearance and be almost dust-free. The dual release and extended release tablets may be less chalky, have increased binding characteristics, and have less attrition and cleaner handling. The dual release and extended release tablets may also possess pleasing aesthetic characteristics. In contrast, without the granulation and heat treatment, the base composition of the dual release and extended release tablets may appear chalky and may be dusty to the touch.

The hardness of tablets may be tested by any standard method that measures the fracturing/breaking point (compressive force) of a tablet. For example, an MHT-100 Portable Hardness Tester manufactured by the Pharma Alliance Group (Valencia, Calif.) may be used. In one embodiment, the tablets may have a hardness of at least about 100 Newtons, at least about 200 Newtons, at least about 300 Newtons, or at least about 400 Newtons.

In one embodiment the tablets may be round with beveled edges of varying thickness and diameter. In another embodiment, the shape may be elongated so as to fit through grates on catch basins. The tablets may be any shape or size desired depending on the selection of the punch and die and the amount of fill material required to achieve the requisite amount of active ingredient and the desired extended release characteristics. As used herein, "tablet" forms include tablets themselves as well as other solid forms or shapes known in the art such as sticks, pucks, briquettes, pellets, beads, spheres, granules, micro-granules, extrudates, cylinders, ingot, and the like. Any shape tablet may be used in accordance with the invention and is only limited by the ingenuity of the tool and die maker.

Without being limited by theory, it is believed that the water-soluble binder combined with the plaster granulates just by heating and applying mechanical force or mixing. Alternatively, the binder and plaster granulates upon heating with or without mixing and with or without applying pressure. Within the temperature and mixing ranges disclosed herein, the powder may granulate without the addition of liquids. It is believed that the plaster, the active ingredient, and the water-soluble binder form a matrix. For example, in one embodiment, the water-soluble binder comprises polyethylene glycol and the plaster comprises plaster of Paris. When the base composition is placed in water, it is believed that the polyethylene glycol dissolves and the plaster of Paris hydrolyzes into gypsum. The gypsum matrix incorporates the active ingredient and is able to hold its shape, which provides the extended release of the active ingredient over a period of time. Without being limited by theory, it is believed that the non-water soluble binder acts to slow down the rate at which the remaining matrix dissolves.

Without being limited by theory, it is believed that many active ingredients cannot be compressed directly into a tablet because they lack the proper characteristics of bonding or binding together. Therefore, additional ingredients such as binders, disintegrants, and lubricants may be added. Furthermore, plaster has been found to be useful in controlling the release of active ingredients in the presence of water.

The compositions of the present invention have sufficient density so that they fill a die to be compressed into a tablet of a desired weight. The dual release tablets may weigh from about 0.5 grams to about 20.0 grams, particularly from about 1.0 gram to about 10.0 grams, and more particularly from about 1.0 gram to about 5.0 grams. The extended release tablets may weigh from about 1.0 gram to about 70 grams, particularly from about 2.5 grams to about 60.0 grams, and more particularly from about 5.0 grams to about 50 grams.

The dual release, extended release, and quick release tablets may be used by, for example, without limitation, placing the tablets in bodies of water. The tablets may also be placed in an area that is intermittently wet. Examples of application sites include, without limitation, marine and freshwater aquatic environments, storm water drainage areas, sewers and catch basins, woodland pools, snow pools, roadside ditches, retention ponds, freshwater dredge spoils, tire tracks, rock holes, pot holes and similar areas subject to holding water; natural and manmade aquatic sites, fish ponds, ornamental ponds and fountains, other artificial water-holding containers or tanks, flooded crypts, transformer vaults, abandoned swimming pools, construction and other natural or manmade depressions, stream eddies, creek edges, and detention ponds; freshwater swamps and marshes including mixed hardwood swamps, cattail marsh, common reed wetland, water hyacinth ponds, and similar freshwater areas with emergent vegetation; brackish water swamps and marshes, intertidal areas; sewage effluent, sewers, sewage lagoons, cesspools, oxidation ponds, septic ditches and tanks, animal waste lagoons and settling ponds, livestock runoff lagoons, wastewater impoundments associated with fruit and vegetable processing, and similar areas. Other examples include, without limitation, dormant rice fields (for application during the interval between harvest and preparation of the field for the next cropping cycle), and in standing water within pastures/hay fields, rangeland, orchards, and citrus groves where mosquito breeding occurs.

In one embodiment, the base composition and the cap composition of the dual release tablets may be formed into a tablet that may be used in potable water, which provides immediate release and extended release of an active ingredient. In another embodiment, the extended release composition may be formed into a tablet that provides a 30 day extended release of an active ingredient. In another embodiment, the composition may be formed into a tablet that provides a 60 day extended release of an active ingredient. In a further embodiment, the composition may be formed into a tablet that provides a 150 day extended release of active ingredient. In yet another embodiment, the tablets may be labeled "organic."

The dual release, quick release, and extended release tablets may be used, without limitation, for plant protection (combating organisms harmful to plants or protecting plants from attack or infestation), controlling or eliminating pests, protecting organic and non-organic materials from pests, protection of animals against pests, water treatment to increase the potability of water, and combinations thereof. Harmful organisms or pests may include, without limitation, weeds, fungi, insects, arachnids or nematodes, bacteria, parasites, protozoans, archaea, protests, amoeba, other microorganisms, and combinations thereof. The tablets may be used to control or eliminate mosquitoes. Mosquitoes are vector agents that may carry disease-causing viruses and parasites, for example, from person to person. Mosquito borne diseases include but are not limited to yellow fever, dengue fever, and malaria. Methods used to prevent the spread of disease may include methods of controlling or eliminating mosquitoes. The tablets may be used in combination with, but not limited to, other pesticides, insecticides, fungicides, nematocides, acaricides, bactericides, algicides, herbicides, germicides, rodenticides, antioxidants, anti-preservatives, biocides, catalysts, chemical reactants, disinfectants, drugs, plant growth regulators, synergists, fertilizers, soil conditioners and/or animal feeds, other agents that benefit the environment of use, and combinations thereof. In one embodiment, the tablet may be used as a water treatment to remove undesired microorganisms. In another embodiment, tablets may remove other impurities and comprise other active agents including, but not limited to, sequestering agents or chelating agents for metal contamination, and flocculants to remove suspended particles. In one embodiment, the dual release, quick release, and extended release tablets are useful for the control of mosquito populations since mosquitoes require water to complete their life cycle. The dual and extended release tablets may provide extended release of an active ingredient when placed in water, for example, during mosquito control application.

EXAMPLES

Exemplary embodiments of the present invention are provided in the following examples. These examples are presented to illustrate the present dual release, quick release, and extended release compositions and to assist one of ordinary skill in making and using the same. The examples are not intended in any way to otherwise limit the scope of the invention.

For the examples below, the technical material, Spinosad NT was supplied by Dow AgroSciences LLC, Indianapolis, Ind. Spinosad NT consists of the active ingredients Spinosyn A and Spinosyn D at a total nominal concentration of 90.4%. It is derived from the metabolites of the naturally occurring bacteria, *Sacchararopolyspora spinosa* and has been shown to be highly effective against a wide variety of insects including species from the orders Coleoptera, Diptera, Hymenoptera, Lepidoptera, and Thysanoptera. The plaster was supplied by United States Gypsum Company, Chicago, Ill. The polyethylene glycol was supplied by Dow Chemical Company, Midland, Mich. and sold under the trademark of Carbowax. It is also available from various distributors and in varying molecular weights. The dicalcium phosphate dihydrate, the magnesium stearate, the citric acid, and the sodium bicarbonate are commodity items and are sold by various suppliers and/or distributors.

Example 1

Extended release tablets were made with the following formulations presented in Table 1 and 2. The compositions were direct compressed on a Carver press at 15,000 lbs or direct compressed on a Stokes press at 30,000 lbs.

TABLE 1

Extended release formulations.

| Component | Sample 1 wt % | Sample 2 wt % |
|---|---|---|
| Spinosad Technical (90.5) | 0.552 | 2.76 |
| No. 1 Moulding Plaster | 0.500 | 3.31 |
| C-Base Plaster | 4.098 | 25.60 |
| Carbowax 8000 | 0.800 | 8.00 |
| Magnesium Stearate | 0.050 | 0.33 |
| Total: | 6.000 | 40.00 |

TABLE 2

Extended release formulations.

| Component | Sample 1 Wt % | Sample 2 Wt % | Sample 3 Wt % | Sample 4 Wt % |
|---|---|---|---|---|
| Spinosad Technical 88.9% | 5.25 | 5.30 | 5.60 | 5.60 |
| No. 1 Moulding Plaster | 84.42 | 85.23 | 0.00 | 83.40 |
| C-Base Plaster | 0.00 | 0.00 | 83.40 | 0.00 |
| Carbowax 1450 | 9.38 | 0.00 | 0.00 | 0.00 |
| Carbowax 3350 | 0.00 | 9.47 | 10.00 | 10.00 |
| Magnesium stearate | 0.95 | 0.00 | 1.00 | 1.00 |
| Total: | 100.00 | 100.00 | 100.00 | 100.00 |

Example 2

A dual release tablet comprising a cap and a base was made with the formulation set forth below in Tables 3 and 4. A cap provides quick release of an active ingredient, and the base provides an extended release of an active ingredient.

TABLE 3

Base formulation.

| Component | Grams | Wt (%) |
|---|---|---|
| Spinosad Tech (90.4%) | 0.100 | 9.452 |
| C-Base Plaster | 0.840 | 79.395 |
| Carbowax 8000 | 0.100 | 9.452 |
| Dicalcium Phosphate Dihydrate | 0.008 | 0.756 |
| Magnesium Stearate | 0.010 | 0.945 |
| Total: | 1.058 | 100.000 |

TABLE 4

Cap formulation.

| Component | Grams | Wt (%) |
|---|---|---|
| Spinosad Tech (90.4%) | 0.012 | 4.110 |
| C-Base Plaster | 0.050 | 17.123 |
| Citric Acid | 0.050 | 17.123 |
| Sodium Bicarbonate | 0.150 | 51.370 |
| Dicalcium Phosphate Dihydrate | 0.030 | 10.274 |
| Total: | 0.292 | 100.000 |

The total grams of material in one tablet were 1.350 grams. The base formulation was heated and appeared to become denser and formed granules. The cap and base ingredients were mixed separately and then directly compressed using a Carver tablet press.

Example 3

A method using heat treatment was developed to improve the flowability of the sample to the tablet press. A base formulation is set forth below in Table 5.

TABLE 5

Base formulation.

| Component | Grams | Wt (%) |
|---|---|---|
| Spinosad Tech (90.4%) | 0.100 | 9.452 |
| C-Base Plaster | 0.840 | 79.395 |
| Carbowax 8000 | 0.100 | 9.452 |
| Dicalcium Phosphate Dihydrate | 0.008 | 0.756 |
| Magnesium Stearate | 0.010 | 0.945 |
| Total: | 1.058 | 100.000 |

The ingredients were added to a 250 mL beaker and then placed in a 75° C. water bath. The formulation was mixed with a spatula by hand during heating. The formulation was heated at 75° C. for one hour, and then the temperature was increased to 80° C. for 30 minutes. The batch did not harden. It remained soft and pliable and appeared to easily granulate.

The granules were screened using U.S.A. standard testing sieves, 8" diameter. The granulated sample was sieved through a 10, 20, 30, 40, 50, and 60 mesh screen.

Example 4

A dual release tablet that may be used in potable water was prepared using +40 mesh heat treated base and a non-heat-treated cap. The cap portion of the tablet comprised 0.29 grams and the heat-treated base comprised 1.058 grams, for a total of 1.348 grams per tablet. The base was poured into a 12 mm diameter beveled flat face die. The die was tapped to level out the base. The die was pressed by hand. The cap was then poured into the die and tapped to level. The die was pressed to 10,000 pounds using a Carver Press, Model C and then released. An Arbor Press 1/2T was used to extract the tablet. The tablet was then placed in a glass jar containing desiccant.

Example 5

Twenty tablets of 30 day extended release tablets were prepared for field trials using the non-heated process and the heated process, with the formulations presented in Tables 6 and 7, respectively. Each tablet weighed 6 g.

TABLE 6

Non-heated 30 day formulation.

| Component | Wt (%) | Grams |
|---|---|---|
| Spinosad Tech | 9.403 | 18.806 |
| No. 1 Moulding plaster | 8.333% | 16.666 |
| C-Base Plaster | 68.098 | 136.196 |
| Carbowax 8000 | 13.333 | 26.666 |
| Magnesium Stearate | 0.833 | 1.666 |
| Total: | 100.00 | 200.00 |

The formulation was blended/ground in a Waring blender at high speed and 80% power in one minute intervals for a total of 2 minutes. Each tablet weighed 6 g.

TABLE 7

Heated 30 day formulation

| Component | Wt (%) | Grams |
|---|---|---|
| Spinosad Tech, 88.6% | 9.403 | 18.806 |
| No. 1 Moulding plaster | 8.333% | 16.666 |
| C-Base Plaster | 68.098 | 136.196 |
| Carbowax 8000 | 13.333 | 26.666 |
| Magnesium Stearate | 0.833 | 1.666 |
| Total: | 100.00 | 200.00 |

The ingredients were weighed into a 600 mL beaker and mixed with a spatula after the addition of each ingredient. The mixing cycles are presented in Table 8. The mixture was poured into a Waring blender that was equipped with heating tapes (Thermolyne/Barnstead, Fibrox Heavy Insulated, 6 ft) that were wrapped around the stainless steel container. The temperature at the start of mixing was 65° C. on the outside.

TABLE 8

Mixing cycles.

| Mix Cycle | Mix Time | Mix Speed as % of voltage regulator | Temperature batch | (Heat) Thermolyne Input Control |
|---|---|---|---|---|
| 1 | 2 min | 80% | 63° C. | #2 |
| 2 | 2 min | 80% | 63° C. | #2 |
| 3 | 2 min | 80% | 63° C. | #2 |
| 4 | 2 min | 60% | — | #2 |
| 5 | 1 min | 50% | — | #3 |
| 6 | 2 min | 50% | — | #3 |
| 7 | 5 min | 50% | — | #4 |
| 8 | 5 min | 50% | 57.8° C. | #5 |

The end temperature was 63° C. The sides of the mixer were scraped down between each mixing cycle. The speed was reduced and the top of the mixer was kept off at cycle #5 where the powder was beginning to granulate. Mixing was stopped after cycle #8 as granules were starting to harden and increase in size.

A Wiley mill and a coffee grinder were used to reduce the particle size of large granules. The granules were screened through 20, 30, 40, 50, and 60 mesh and −60 mesh (pan) sieves (Table 9).

TABLE 9

Sieve analysis.

| Sieve Size | Grams |
|---|---|
| +20 mesh | 10.12 |
| +30 mesh | 15.28 |
| +40 mesh | 72.91 |
| +50 mesh | 20.75 |
| +60 mesh | 6.53 |
| −60 mesh | 48.14 |
| | (remaining in pan) |
| Total: | 86.87% recovery |

Example 6

Twenty tablets of 150 day extended release tablets were prepared for field trials using the non-heated process and the heated process, with formulations presented in Tables 10 and 11, respectively. Each tablet weighed 40 g.

TABLE 10

Non-heated 150 day formulation.

| Component | Wt (%) | Grams |
|---|---|---|
| Spinosad Tech | 7.055 | 84.660 |
| No. 1 Moulding plaster | 8.275 | 99.300 |
| C-Base Plaster | 64.340 | 772.080 |
| Carbowax 8000 | 20.00 | 240.000 |
| Magnesium Stearate | 0.330 | 3.960 |
| Total: | 100.00 | 1200.00 |

The ingredients were weighed into a KitchenAid® mixing bowl and mixed for 5 minutes using a paddle stirrer at the #2 setting. The batch was divided into 300 gram increments and ground in a Waring blender at low speed and 96% powder for 2 cycles of 1 minute each. The mixture was poured back into the KitchenAid® mixing bowl and mixed for 5 additional minutes using a paddle stirrer at the #2 setting. The recovery was 1186.8 grams, or 98.9%. 40 grams of powder was weighed out and pressed into a tablet.

TABLE 11

Heated 150 day formulation.

| Component | Wt (%) | Grams |
|---|---|---|
| Spinosad Tech | 7.055 | 84.660 |
| No. 1 Moulding plaster | 8.275 | 99.300 |
| C-Base Plaster | 64.340 | 772.080 |
| Carbowax 8000 | 20.00 | 240.000 |
| Magnesium Stearate | 0.330 | 3.960 |
| Total: | 100.00 | 1200.00 |

Barnstead/Thermolyne (Fibrox, heavy insulated, 6 ft) heating tapes were applied to a KitchenAid® mixing bowl using Nashua® Extreme Weather foil backed tape (rated to 260° F.). The mixing bowl was preheated (#3 on Thermolyne input control, type 45500).

The ingredients were weighed separately and added to the mixing bowl. The temperature of the heating tape was at #3, or 60° C. Using a paddle mixer, the batch was mixed for 10 minutes on the "stir" cycle of KitchenAid®. The batch temperature was 34.9° C. The mixing blade was switched to a wire whisk and the temperature was increased to #4 on the Thermolyne input controller. The temperature was 79° C. The batch was mixed for 10 minutes on the #2 cycle of KitchenAid®. The batch temperature was 39° C. The temperature was increased to #5 on the Thermolyne input controller and the mixing was continued on the #2 cycle. The powder was turning to paste along the walls of the mixing bowl, so the sides were scraped about every 2 minutes of mixing. The speed of the mixing was slowly increased as the powder began to granulate. The total mixing time was approximately 1 hour.

The granules were screened through 20, 30, 40, 50, and 60 mesh sieves. The larger particles were ground in a Wiley mill and then re-sieved.

TABLE 12

Sieve analysis.

| Sieve Size | Grams | To make a 40 gram tablet the following factions were used (g/batch) | % of sieved granules |
|---|---|---|---|
| +12 mesh | 176.14 | 0.00 | 0.00 |
| +20 mesh | 274.54 | 150.15 | 28.14 |
| +30 mesh | 228.08 | 228.08 | 42.74 |
| +40 mesh | 81.06 | 81.06 | 15.19 |
| +50 mesh | 54.31 | 54.31 | 10.18 |
| +60 mesh | 28.00 | 20.00 | 3.75 |
| −60 mesh | 170.00 | 0.00 | 0.00 |
| Total: | 84.34% recovery | 533.60 | 100.00 |

The granules used for a 150 day tablet are described in Table 12 above. 533.60 grams made 13 tablets.

Example 7

30 day extended release tablets were prepared as set forth below in Tables 13-15. Each tablet weighed 6 g.

TABLE 13

30 day formulation.

| Component | Wt (%) | Grams |
|---|---|---|
| Spinosad Tech, 88.6% | 9.403 | 28.209 |
| No. 1 Moulding plaster | 8.333 | 24.999 |
| C-Base Plaster | 68.098 | 204.294 |
| Carbowax 8000 | 13.333 | 39.999 |
| Magnesium Stearate | 0.833 | 2.499 |
| Total: | 100.00 | 300.00 |

TABLE 14

Mixing cycles.

| Mix Cycle | Mix Time | Mix Speed as % of voltage regulator | Temperature batch | (Heat) Thermolyne Input Control |
|---|---|---|---|---|
| Initial | — | — | 23.7° C. | — |
| 1 | 2 min | 50% | 52.4° C. | (start at #3) #3 |
| 2 | 1 min | 80% | 55.8° C. | #3 |
| 3 | 1 min | 80% | 59.1° C. | #3 |
| 4 | 6 min | 50% | 63.2° C. | #3 |

The formulation was sieved by hand (Table 15). The +30 and +40 mesh fractions were mixed together and were used to press into 6 gram tablets having a 22 mm diameter.

TABLE 15

Sieve analysis.

| Sieve Size | Grams |
|---|---|
| +20 mesh | 28.64 |
| +30 mesh +40 mesh | 74.53 |
| +50 mesh | 29.24 |
| +60 mesh | 98.94 |
| −60 mesh | 64.27 |

Example 8

A 150 day extended release tablet was formulated as set forth below in Tables 16-18. Each tablet weighed 40 g.

TABLE 16

150 day formulation.

| Component | Wt (%) | Grams |
|---|---|---|
| Spinosad Tech, 88.6% | 7.055 | 32.275 |
| No. 1 Moulding plaster | 8.275 | 41.375 |
| C-Base Plaster | 64.340 | 321.700 |
| Carbowax 3350 | 20.000 | 100.000 |
| Magnesium Stearate | 0.330 | 1.650 |
| Total: | 100.00 | 500.000 |

The ingredients were weighed into a 1 quart glass measuring container and mixed by hand using a spatula. Mixing cycles are presented in Table 17. The mixture was poured into a 1 liter stainless steel dry blending container that was equipped with heating tapes (Thermolyne/Barnstead, Fibrox heavy insulated, 6 ft) wrapped around the outer part of the container. The mixture was mixed for a total of 2 minutes in 1 minute intervals before heating was started. Half of the batch was processed at a time so as not to overload the mixer. 250 grams of powder were removed before heating.

TABLE 17

Mixing cycles.

| Mix Cycle | Mix Time | Mix Speed as % of voltage regulator | Temperature batch | (Heat) Thermolyne Input Control |
|---|---|---|---|---|
| 1 | 2 min | 80% | 48.4° C. | #2 |
| 2 | 1 min | 80% | 52.8° C. | #2 |
| 3 | 1 min | 80% | 56.9° C. | #3 |
| 4 | 1 min | 80% | 59.1° C. | #3 |
| 5 | 6 min | 50% | 65.0° C. | #3 |

The formulation was screened by hand, using 8" diameter USA Standard test sieves.

TABLE 18

Sieve analysis.

| Sieve Size | Grams |
|---|---|
| +16 mesh | 22.77 |
| +30 mesh +40 mesh +50 mesh | 117.44 |
| −50 mesh | 81.57 |
| Total | 221.78 (out of 250 = 88.71%) |

Example 9

A 150 day extended release tablet was formulated as set forth below in Tables 19-21.

TABLE 19

150-day formulation.

| Component | Wt (%) | Grams |
|---|---|---|
| Spinosad Tech | 7.055 | 21.165 |
| USG #1 Molding plaster | 8.275 | 24.825 |

TABLE 19-continued

| 150-day formulation. | | |
|---|---|---|
| Component | Wt (%) | Grams |
| C-Base Plaster | 64.340 | 193.020 |
| Carbowax 3350 | 20.000 | 60.000 |
| Magnesium Stearate | 0.330 | 0.990 |
| Total: | 100.00 | 300.000 |

To make a 40 gram tablet at 6.25%, 200 grams were needed. Two 300 gram batches were prepared.

The ingredients were weighed into a 600 mL beaker and blended with a spatula after the addition of each ingredient. Mixing cycles are presented in Table 20. The mixture was poured into a 1 liter stainless steel Waring blender (old model with no handle) that was equipped with heating tapes as described in Example 8. Heating was not started until after 1 minute of mixing. The formulation was sieved by hand (Table 21).

TABLE 20

| Mixing cycles. | | | | |
|---|---|---|---|---|
| Mix Cycle | Mix Time | Mix Speed as % of voltage regulator | Temperature batch | (Heat) Thermolyne Input Control |
| 1 | 1 min | 100% | 36.4° C. | 0 |
| 2 | 1 min | 110% | 44.3° C. | Start at #2 |
| 3 | 1 min | 110% | 52.3° C. | #2 |
| 4 | 1 min | 110% | 58.6° C. | #2 |

TABLE 21

| Sieve analysis. | |
|---|---|
| Sieve Size | Grams |
| +16 mesh | 98.68 |
| +30 mesh +40 mesh +50 mesh | 126.91 |
| −50 mesh | 47.66 |
| Total | 273.25 (out of 300 = 91.08%) |

Example 10

A 150 day extended release tablet was formulated as set forth below in Tables 22-24.

TABLE 22

| 150 day formulation | | |
|---|---|---|
| Component | Wt (%) | Grams |
| Spinosad Tech, 88.6% | 7.055 | 21.165 |
| No. 1 Moulding plaster | 8.275 | 24.825 |
| C-Base Plaster | 64.340 | 193.020 |
| Carbowax 3350 | 10.000 | 30.000 |
| Carbowax 8000 | 10.000 | 30.000 |
| Magnesium Stearate | 0.330 | 0.990 |
| Total: | 100.00 | 300.000 |

To make a 40 gram tablet at 6.25%, 200 grams were needed, therefore another 300 gram batch was prepared.

The ingredients were weighed into a 600 mL beaker and blended with a spatula after the addition of each ingredient. The mixture was poured into a 1 liter stainless steel Waring blender that was equipped with heating tapes as described in Example 8.

TABLE 23

| Mixing cycles. | | | | |
|---|---|---|---|---|
| Mix Cycle | Mix Time | Mix Speed as % of voltage regulator | Temperature batch | (Heat) Thermolyne Input Control |
| 1 | 1 min | 110% | 36.1° C. | 0 |
| 2 | 1 min | 110% | 41.0° C. | Start at #2 |
| 3 | 1 min | 45% | 45.6° C. | #2 |
| 4 | 1 min | 45% | 53.8° C. | #2 |
| 5 | Continuous | 45% | 59.6° C. | #3 |
| 6 | While granulatingg | 45% | 62.0° C. | #3 |

TABLE 24

| Sieve analysis. | |
|---|---|
| Sieve Size | Grams |
| +16 mesh | 39.24 |
| +30 mesh +40 mesh +50 mesh | 169.79 |
| −50 mesh | 31.68 |
| Total | 240.71 (recovery = 80.24%) |

Example 11

A 200 gram sample of the dual release tablet base (which may be used for potable water) and a 30 day tablet were prepared as set forth in Tables 25 and 26, respectively, to measure the physical properties.

TABLE 25

| Dual release tablet base. | | | |
|---|---|---|---|
| Component | Wt (%) | Grams/tablet | gms/batch |
| Spinosad Tech, 88.6% | 9.639 | 0.102 | 19.28 |
| C-Base Plaster | 79.208 | 0.838 | 158.42 |
| Carbowax 8000 | 9.452 | 0.100 | 18.90 |
| Dicalcium Phosphate Dihydrate (DCP) | 0.756 | 0.008 | 1.51 |
| [Magnesium Stearate] | 0.945 | 0.010 | 1.89 |
| Total: | 100.00 | 1.058 | 200.00 |

The C-Base, Spinosad, Carbowax, and DCP were weighed into a 1 liter stainless steel Waring blender. The blender was run for 30 seconds on rheostat at 70%. The sides were scraped down and the blender was run for an additional 30 seconds. Recovery was 196.74 grams per 198.11 grams, or 99.31%.

TABLE 26

| 30 day tablet. | | | |
|---|---|---|---|
| Component | Wt (%) | Grams/tablet | Gms/batch |
| Spinosad Tech, 88.6% | 9.403 | 0.564 | 18.81 |
| USG #1 Molding Plaster | 8.333 | 0.500 | 16.67 |
| C-Base Plaster | 68.098 | 4.086 | 136.20 |

TABLE 26-continued 30 day tablet.

| Component | Wt (%) | Grams/tablet | Gms/batch |
|---|---|---|---|
| Carbowax 8000 | 13.333 | 0.800 | 26.67 |
| [Magnesium Stearate] | 0.833 | 0.050 | 1.67 (not added) |
| Total: | 100.00 | 6.000 | 200.00 |

The C-Base, Spinosad, and Carbowax were weighed into a 1 liter stainless steel waring blender. The blender was run for 30 seconds on rheostat at 70%. The sides were scraped down and the blender was run for an additional 30 seconds. Recovery was 197.33 grams per 198.33 grams, or 99.50%.

Example 12

An extended release tablet was prepared as set forth below in Tables 27-30.

TABLE 27

Base formulation.

| Component | Wt (%) | Grams/tablet |
|---|---|---|
| Spinosad Tech (88.60%) | 9.369 | 0.102 |
| C-Base Plaster | 79.208 | 0.838 |
| Carbowax 8000 | 9.452 | 0.100 |
| Dicalcium Phosphate Dihydrate | 0.756 | 0.008 |
| Magnesium Stearate | 0.945 | 0.010 |
| Total: | 100.00 | 1.058 |

TABLE 28

Cap formulation.

| Component | Wt (%) | Grams/tablet |
|---|---|---|
| Spinosad Tech (88.60%) | 4.223 | 0.0122 |
| C-Base Plaster | 16.423 | 0.0476 |
| Citric Acid | 17.251 | 0.0500 |
| Sodium Bicarbonate | 51.753 | 0.1500 |
| Dicalcium Phosphate Dihydrate | 10.350 | 0.0300 |
| Total: | 100.00 | 0.2898 |

The cap was prepared first (Table 28). Inert ingredients were stored at 50° C. except for technical material. Each ingredient was weighed into a 1 liter stainless steel waring blender and mixed for 30 seconds (rheostat=30, blender=#7). The sides of the blender were wiped down and the formulation was mixed for another 30 seconds and the sides were again wiped down. A final mix was conducted for 1 minute (rheostat=50, blender=#7). The mixture was poured into an eight ounce wide mouth jar. The recovery was 115.44 grams per 115.92 grams of the batch, or 99.59%.

Next, the heat treated base was prepared (Table 27). The ingredients were weighed into a 600 mL beaker and mixed with a spatula. The mixture was poured into a 1 liter stainless steel waring blender that was equipped with heating tapes (Thermolyne/Barnstead, Fibrox heavy insulated, 6 ft) that were wrapped around the blender. The blended powders were poured into the blender and heating was started.

TABLE 29

Mixing cycles.

| Mix Cycle | Mix Time | Mix Speed as % of voltage regulator | Temperature batch | (Heat) Thermolyne Input Control |
|---|---|---|---|---|
| Initial | — | — | 24° C. | #3 |
| 1 | 2 min | 80% | 53.8° C. | #3 |
| 2 | 1 min | 80% | 61.0° C. | #3 |
| 3 | 1 min | 80% | 63.0° C. | #2 |
| 4 | 8 min | 50% | 63.2° C. | #2 |
| 5 | 5 min | 50% | 63.2° C. | #3 |

TABLE 30

Sieve analysis.

| Sieve Size | Grams |
|---|---|
| +12 mesh | 3.99 |
| +20 mesh | 101.67 |
| +30 mesh | 89.83 |
| +40 mesh | 51.01 |
| +60 mesh | 19.56 |
| −60 mesh | 21.93 |
| Total | 284.00 (out of 300 = 94.67%) |

A base sample was prepared using the +30 mesh, +40 mesh, and +60 mesh, for a total of 160.40 grams.

The cap sample was stored in the 50° C. oven when not in use. The base sample was stored at room temperature. The tablet was prepared as follows. A complete tablet (assay should be 7.50%±5%) included 0.29 grams of the cap sample and 1.058 grams of the base sample for a total of 1.348 grams. The tablet was made by pouring the base into a 12 mm diameter beveled flat face die. The die was tapped to level out the base powder and was pressed by hand. The cap was poured into the die on top of the base and tapped to level. It was pressed to 10,000 pounds using a Carver Press (model C s/n 34000/486) and then released. An Arbor Press (½ ton) was used to extract the tablet. The tablets were placed in a glass jar containing desiccant. Assay cap powder was 3.78% (target 3.74%) and the assay base granules were 8.67% (target 8.54%).

Example 13

A 45 pound batch of base was prepared as set forth below in Tables 31-32 using a Ribbon Blender (Ross Model RB 42A-1 s/n 39786).

TABLE 31

Base formulation.

| Component | Wt (%) | 45 lb batch |
|---|---|---|
| Spinosad Tech (88.60%) | 9.66 | 4.35 |
| C-Base Plaster | 79.18 | 35.63 |
| Carbowax 8000 | 9.45 | 4.25 |
| Dicalcium Phosphate Dihydrate | 0.76 | 0.34 |
| Magnesium Stearate | 0.95 | 0.43 (hold) |
| Total: | 100.00 | 45.00 |

The Spinosad, Carbowax, and DCP were weighed into small containers and preheated in a 45° C. oven. The C-Base plaster was weighed into a 5 gallon pail. The plaster was poured into a 1.0 cubic foot Charles Ross Ribbon blender (Model RB 42A-1, s/n 39786). Before loading the blender, Thermo Scientific Brisk Heat Heating tapes with controller were taped onto the sides. The size was 1 inch wide by 10 feet long. A thermometer was taped on the inside front and the back side and heating measurements were taken to ensure the correct heat could be obtained (60° C.-63° C.).

The heat tapes appeared to provide enough heat for granulation of the base powder. Only one set of heat tapes was used. The ribbon blender was emptied.

TABLE 32

Temperatures.

| | |
|---|---|
| 2:00 pm | Load blender, heat tape at 50% of controller |
| 2:45 pm | Batch temp was 40° C. This was not enough heat, so the outside heaters were mounted at the back and front of the mixer and put at the highest setting. |
| 2:55 pm | Batch temp was 47° C. The heat tape was increased to 100% of the controller |
| 3:15 pm | Batch temp was 51° C. |
| 3:30 pm | Batch temp was 56.5° C. |
| 3:45 pm | Batch temp was 58° C. |
| 4:00 pm | Batch temp was 59.3° C. (small clumps formed on the left and right corners) |
| 4:15 pm | Batch temp was 60.3° C. (beginning to granulate so mixing was continued until 4:45 pm, then discontinued and the sample was discharged). |

The +10 mesh fraction was sieved off and run through a hammer mill, Bantam Mikro Pulverizer (Type CF s/s, s/n 72-J-1322) without a screen to reduce larger sized particles. Then the sample was screened using a −20 and a +60 mesh sieve to use for tabletting. 5.1 lbs was used to make the sample. This was multiplied by 0.95% for the Mg stearate amount. 22.15 grams of Mg stearate were dusted onto this −20+60 mesh sample using a 50 mesh sieve and mixed in a 8¼ quart stainless steel beaker.

Example 14

A 50 pound batch of base (30 day tablet) was prepared using a Ribbon Blender. The blender was equipped with a set of heating tapes on either side (front and back). The tapes were Thermo Scientific, Brisk Heat heating tapes (controller s/n 89659/4).

A 30 day tablet (6 grams) was prepared as follows in Tables 33-35.

TABLE 33

Base formulation.

| Component | Wt (%) | 50 lb batch |
|---|---|---|
| Spinosad Tech (88.60%) | 9.50 | 4.8 |
| No. 1 Moulding plaster | 8.33 | 4.2 |
| C-Base Plaster | 68.00 | 34.0 |
| Carbowax 8000 | 13.33 | 6.7 |
| Magnesium Stearate (sprinkle on after ingredients mixed) | 0.83 | 0.4 |
| Total: | 100.00 | 50.00 |

The C-Base plaster, No. 1 Moulding plaster, and Carbowax were weighed into a 5 gallon pail (inerts). The tech was weighed into a 2.5 gallon pail and placed in a 50° C. oven. The temperature of the inerts was 24° C. They were poured into a Ross 1.0 cubic foot ribbon blender, Model RB42A-1. The temperature of the tech was 25° C. It was poured into the blender and mixing was begun. The heating tapes were set at 35% of the control. After 15 minutes of mixing, the mixer was stopped and the temperature was 28° C. After 30 minutes of mixing, the mixer was stopped and the temperature was 38° C. The temperature of the heat tapes was increased to 45% of the control. After 45 minutes of mixing, the mixer was stopped and the temperature was 43° C. The sides were scraped with a 1.5" paint brush. The batch was still in the powder state. After 60 minutes of mixing, the mixer was stopped and the temperature was 47° C. The sides were brushed down. The temperature of the heat tapes was increased to 50% of the control. After 1.5 hours the temperature was 56° C. There was some observable melting appearing in the front corner of the blender. The temperature of the heating tapes was lowered to 45% of control. The batch appeared to be densifying after 1.5 hours mixing and 56° C. After an additional 10 minutes, the temperature of the heating tapes was turned down to 35% of control, then 10 more minutes of mixing, followed by scraping of the sides. The temperature was lowered to 15% of control. After 10 additional minutes the temperature was lowered to 5% of control as the sample had begun densifying and sticking to the far wall of the blender. After 10 more minutes, the blender was stopped, the sides scraped down, the heating stopped, and a cooling fan was applied to the back of the blender. The batch was allowed to cool with mixing for approximately 15 minutes, then the mixing was stopped and clumps were broken up (product warm, but not hot). The product was discharged into 2 trays. Recovery was 98.99%. There was some material left in the blender that had adhered to the walls. The larger, possibly unusable chunks were sieved off. The first cut was to sieve off all sample that was +4 mesh using 8" diameter sieves that were screened by hand.

Tablets were made using the −20+60 mesh fraction (23.68 lbs). See Table 34 for sieve analysis. 0.83% of magnesium stearate was added so that the tablet would not stick in the tablet press. It was sifted onto the sample using a 50 mesh screen. A 6 gram tablet (beveled edge), 25 mm wide by 6.5 mm deep, was made using an Adept Engineers Rotary Tablet Press

TABLE 34

Sieve analysis of the 50 lb batch of 30 day granules.

| Sieve Size | Pounds | % |
|---|---|---|
| +4 mesh | 15.22 | 31.28 |
| +10 mesh | 9.57 | 19.67 |
| +20 mesh | 11.16 | 22.94 |
| −60 mesh | 1.18 | 2.43 |
| −20 +60 mesh | 11.52 | 23.68 |
| Total | 48.65 | 100 |

773 tablets were made with 143.82 grams of powder left over and 28 tablets were made at initial start up to define the parameters of the tablet press.

The sieve analysis for the granulated base is as follows in Table 35:

TABLE 35

Sieve analysis.

| Sieve Size | Pounds | % |
|---|---|---|
| +4 mesh | 24.84 | 58.57 |
| +10 mesh | 1.17 | 2.76 |

TABLE 35-continued

Sieve analysis.

| Sieve Size | Pounds | % |
| --- | --- | --- |
| −10 + 20 mesh | 1.61 | 3.80 |
| +20 mesh | 2.73 | 6.44 |
| −60 mesh | 6.96 | 16.41 |
| −20 + 60 product | 5.1 | 12.02 |
| Total | 42.41 | 100.00 |

The cap (0.29 grams) was prepared as follows in Table 36. The materials were stored in a 45° C. oven to keep them dry.

TABLE 36

Cap formulation.

| Component | Wt (%) | Grams per batch |
| --- | --- | --- |
| Spinosad Tech (88.60%) | 4.23 | 27.50 |
| C-Base Plaster | 16.42 | 106.72 |
| Citric Acid | 17.25 | 112.13 |
| Sodium Bicarbonate | 51.75 | 336.38 |
| Dicalcium Phosphate Dihydrate | 10.35 | 67.28 |
| Total: | 100.00 | 650.00 |

The ingredients were weighed into a 1 liter stainless steel Waring dry blending container. The batch was blended at the highest speed in 30 second intervals. After each interval the sides were scraped down. The mixture was blended for 5 intervals, and then poured into a 1 quart wide mouth glass jar. Recovery was 641.17 g or 99.56%.

A scored, bi-layer tablet was then made. 1.058 grams of the base were combined with 0.29 grams of the cap for a 1.348 gram tablet. An Adept Engineers 23 station rotary tablet press was used to make the tablet.

Example 15

A 50 pound batch of extended release tablet (150 day) was prepared to make 40 gram tablets as in Table 37.

TABLE 37

Base formulation.

| Component | Wt (%) | Pounds per batch |
| --- | --- | --- |
| Spinosad Tech(88.60%) | 7.10 | 3.6 |
| No. 1 Moulding plaster | 8.27 | 4.1 |
| C-Base plaster | 64.30 | 32.2 |
| Carbowax 8000 | 20.00 | 10.0 |
| Magnesium stearate (sprinkled on after ingredients mixed) | 0.33 | 0.2 |
| Total: | 100 | 50.0 |

The C-Base, molding plaster, and Carbowax (inerts) were weighed into a 5 gallon pail and placed in a 45° C. oven to preheat overnight. The Spinosad was weighed into a 4 quart pail and placed in a 45° C. oven in the morning (the technical material was not preheated overnight). The inerts were loaded into a Ross Ribbon Blender, 1.0 cubic foot, equipped with a set of Thermo Scientific Brisk Heat heating tapes with controller on the back and front of the outside of blender, each measuring 1" wide by 10' long). The temperature of the inerts in the oven was 42° C. The temperature of the Spinosad in the oven was 37° C. The inerts were added to the blender and mixed for 5 minutes, and then the Spinosad was added and mixed for 2 more minutes. Heating was then begun. The temperature of the batch was 30° C. The heat tapes were set at 25° C. After 15 minutes of heating and mixing, the batch temperature was measured to be 34° C. and the sides were scraped down. After 30 minutes of heating and mixing the batch temperature was 35° C. The heat tape setting was increased to 50%. After 45 minutes of heating and mixing the batch temperature was 40° C. After 60 minutes of heating and mixing the batch temperature was 48° C. After 1.5 hours of heating and mixing the batch temperature was 52° C. After an additional 15 minutes, the batch was beginning to density. The mixer was intermittently turned off and the walls were scraped down. The mixer shut down due to excessive torque requirements on the motor. The batch was not entirely granulated, however, the larger chunks (+4 mesh) were screened off using the 8" diameter sieves.

Recovery of the +4 mesh particles was as follows in Table 38:

TABLE 38

Recovery.

| +4 mesh | 12.28 lbs | 24.59% |
| --- | --- | --- |
| −4 mesh | 37.66 lbs | 75.41% |
| Total | 49.94 lbs | 100% |

Next, the +20 mesh particle size was screened off using an 8" diameter sieve. 21.18 lbs were recovered.

The −20 mesh fraction, weighing 21.18 pounds was sieved to remove the fines. The fines for this product was −60 mesh and weighed 9.75 lbs.

Final tabulation of the sample is as follows in Table 39.

TABLE 39

Sieve analysis.

| +4 mesh | 12.28 lbs |
| --- | --- |
| −4 mesh | This fraction, which was 37.66, was sieved again so there was no remaining fraction. It was contained within the +20 mesh |
| +20 mesh | 16.40 lbs |
| −20 mesh | 21.18 lbs (this fraction was sieved to remove fines) |
| −20 + 60 mesh product | 12.17 lbs |

This provided a total amount of 12.16 pounds of granulated/heated product which could make about 138 tablets (at 40 grams/tablet).

Example 16

TABLE 40

Cap formulation.

| Component | Wt (%) | Grams per batch |
| --- | --- | --- |
| Spinosad Tech (88.60%) | 4.23 | 27.50 |
| C-Base Plaster | 16.42 | 106.72 |
| Citric Acid | 17.25 | 112.13 |
| Sodium Bicarbonate | 51.75 | 336.38 |
| Dicalcium Phosphate Dihydrate | 10.35 | 67.28 |
| Total: | 100.00 | 650.00 |

The cap formulation was mixed according to Table 40. The cap sample was placed into a 170×90 Pyrex crystallizing dish in a 50° C. oven overnight to ensure the sample was dry.

TABLE 41

Base formulation.

| Component | Wt (%) | Grams per batch |
|---|---|---|
| Spinosad Tech (88.60%) | 9.66 | 28.98 |
| C-Base Plaster | 79.18 | 237.54 |
| Carbowax 8000 | 9.45 | 28.35 |
| DCP | 0.76 | 28.35 |
| Magnesium stearate | 0.95 | 2.85 |
| Total | 100.00 | 300.00 |

The ingredients were weighed into a 600 mL beaker and mixed with a spatula. They were poured into a 1 liter stainless steel Waring blender equipped with heating tapes (Thermolyne/Barnstead Fibrox Heating Insulated, 6 ft) that were wrapped around the blender and secured with Extreme Weather 330 foil backed tape. The blended powders were poured into the Waring blender and heating was begun. Mixing cycles are presented in Table 42.

TABLE 42

Mixing cycles.

| Mix Cycle | Mix Time | Mix Speed as % of voltage regulator | Temperature batch | (Heat) Thermolyne Input Control |
|---|---|---|---|---|
| Initial | — | — | 22.6° C. | — |
| 1 | 2 min | 80% | 45.1° C. | #3 |
| 2 | 1 min | 80% | 57.0° C. | #3 |
| 3 | 30 sec | 80% | 58.9° C. | #3 |
| 4 | 30 sec | 80% | 63.5° C. | #3 |
| 5 | 30 sec | 80% | 64.8° C. | #3 |

While the sample was still warm and most of the powder had become granular, it was screened through a 20 mesh sieve, forced through openings with hand pressure. Recovery: The +20 mesh material was placed back in a 50° C. oven. −20+60 mesh=181.35 grams. −60 mesh was 15.55 grams.

The tablet was prepared by mixing 0.29 grams of the cap sample (Table 40) with 1.058 grams of the similarly-prepared base (Table 41) to make a 1.348 gram tablet. The base was poured into a 12 mm beveled flat face die. The die was tapped to level out the base sample and was pressed by hand. The cap was poured into the die on top of the base and tapped to level. It was pressed to 10,000 pounds using a Carver press (Model C, s/n 34000/486), then released and an Arbor Press (½ ton model) was used to extract the tablet. The tablets were placed in a glass jar containing desiccant packs.

Example 17

30 day extended release tablets were prepared as follows. Three batches of 300 grams each were made and then combined into a single batch. The magnesium stearate was added to the single batch.

A 30 day tablet (6 grams) was prepared as follows in Table 43.

TABLE 43

Base formulation.

| Component | Wt (%) | Grams/batch |
|---|---|---|
| Spinosad Tech (88.60%) | 9.40 | 28.21 |
| No. 1 Moulding plaster | 8.33 | 25.00 |
| C-Base Plaster | 68.10 | 204.29 |
| Carbowax 8000 | 13.33 | 40.00 |
| Magnesium Stearate (sprinkle on after ingredients mixed and pregranulated) | 0.83 | 2.50 |
| Total: | 100.00 | 300.00 |

The ingredients were weighed into a 600 mL glass beaker and mixed with a spatula after the addition of each ingredient. They were poured into a 1 liter stainless steel Waring blender that was equipped with heating tapes (Thermolyne/Barnstead, Fibrox heavy insulated, 6 ft) that were wrapped around the blender and secured to the sides with high heat tape. The tablets were prepared as described above in Example 6. The recoveries were as follows in Table 44.

TABLE 44

Recovery.

| | Batch 1 | Batch 2 | Batch 3 | Totals |
|---|---|---|---|---|
| −16 + 60 mesh (product) | 199.49 g | 227.87 g | 192.28 g | 614.64 g |
| +16 mesh (overs) | 70.51 g | 19.82 g | 72.15 g | 162.48 g |
| −60 mesh (fines) | 13.53 g | 35.59 g | 27.84 g | 76.96 g |
| % recovery (total) | 94.51% | 92.76% | 97.42% | 94.90% |
| % recovery (product) | 66.50% | 74.29% | 64.09% | 68.29% |

All of the product (−16+60 mesh) was poured into a 9"×13" glass Pyrex dish and dusted with Mg stearate using a 30 mesh hand sifter. 4.92 grams of Mg stearate were used. The tablets (6 gms each) were pressed with a Carver Press C at 8000 lbs using a flat face die.

Example 18

Eight batches (Tables 45 and 46) of base were made for a potable water tablet base (1.058 grams). The nominal concentration was 8.54% (range 8.113% to 8.967%), and a 2% excess was added to ensure the active ingredient was within the specification. Magnesium stearate was added after granulation.
Batch 1

TABLE 45

Batch 1 Base formulation.

| Component | Wt (%) | lbs/batch |
|---|---|---|
| Spinosad Tech (88.60%) | 9.83 | 5.41 |
| C-Base Plaster | 79.02 | 43.46 |
| Carbowax 8000 | 9.45 | 5.20 |
| DCP | 0.76 | 0.42 |
| Magnesium stearate (not added) | 0.95 | 0.52 |
| Total: | 100.00 | 55.00 |

The C-Base plaster was weighed into a 5 gallon pail. The Spinosad was weighed into a 6 liter pail, the Carbowax into a 4 quart pail and the DCP into an 800 mL tri-cornered polypropylene beaker. Half of the amount of plaster was charged to the Ribbon blender and then the Spinosad, the Carbowax, and the DCP were charged. Finally, the remaining half of the plaster was charged. The mixer top was covered and the ingredients mixed for 20 minutes. The mixture was discharged at the bottom of the mixer by opening the gate valve. The discharge container was not large enough and much of the sample was lost. Recovery was 51.74 pounds.

Batches 2-8

Batches 2-8 were made using the following procedure. The C-Base plaster was weighed into a 5 gallon pail. The Spinosad was weighed into a 6 liter pail, the Carbowax into a 4 quart pail, and the DCP into an 800 mL tri-cornered polypropylene beaker. Half of the amount of plaster was charged to the Ribbon Blender and then the Spinosad, the Carbowax, and the DCP were charged. Finally, the remaining half of the plaster was charged. The mixer top was covered and the ingredients mixed for 20 minutes. The mixture was discharged at the bottom of the mixer by opening the gate valve. The mixture was discharged into a 14 gallon, 21" L×15" W plastic container. Once all of the sample was discharged from the blender into a 14 gallon container, it was poured into a 30 gallon fiber drum that was lined with 2 bags of polyethylene. Approximately 150 lbs of the sample was placed into each of three fiber drums.

TABLE 46

Batches 2-8 Base formulations.

| Component | Wt (%) | grams | lbs/55 lb batch |
|---|---|---|---|
| Spinosad Tech (88.60%) | 9.83 | 0.102 | 5.41 |
| C-Base Plaster | 79.01 | 0.838 | 43.46 |
| Carbowax 8000 | 9.45 | 0.100 | 5.20 |
| DCP | 0.76 | 0.008 | 0.42 |
| Magnesium stearate (not added) | 0.95 | 0.010 | 0.52 |
| Total: | 100.00 | 1.058 | 55.00 |

Example 19

Eight batches (Table 47) of base with 55 lbs per batch were made for a 30 day tablet (6 grams). The nominal active ingredient was 8.33% (range 7.91% to 8.75%), and a 2% excess was added to ensure the active ingredient was within the specification. Magnesium stearate was added after the formation of granules.

The batches were prepared using the following method. The C-Base plaster was weighed into two 5 gallon pails, the #1 Molding plaster was weighed into a 4 quart pail, the Carbowax into two 4 quart pails, and the Spinosad into a 6 liter pail. One of the pails of the C-Base plaster was charged into a Ribbon Blender (Model RB-42-A-1, s/n 39786), then the Spinosad was charged, followed by the Carbowax, the #1 Molding plaster, and the remainder of the C-Base plaster. The mixer top was covered and the ingredients mixed for 20 minutes. The mixture was discharged into a 14 gallon, 21" L×15" W plastic container. Once all of the sample was discharged from the blender into the 14 gallon container, the sample was poured into a 30 gallon fiber drum that was lined with 2 polyethylene bags. The target was 150 pounds per drum.

TABLE 47

Batches 1-8 formulations.

| Component | Wt (%) | lbs/batch |
|---|---|---|
| Spinosad Tech (88.60%) | 9.59 | 5.27 |
| No. 1 Moulding Plaster | 8.33 | 4.58 |
| C-Base Plaster | 67.91 | 37.35 |
| Carbowax 8000 | 13.33 | 7.33 |
| Mg Stearate (not added) | 0.83 | 0.46 |
| Total: | 100.00 | 55.00 |

*Note: Because Mg stearate is not added, active ingredient = 8.57%.

Example 20

A 30 day extended release tablet is prepared as follows in Table 48. The pre-mixed powder is dry granulated using heat (60-63° C.) and mixing to improve flowability to the tablet press. The granules are screened to a particle size range of −20+40 mesh. The formulation is as follows:

TABLE 48

Formulation.

| Ingredient | Approximate Weight % |
|---|---|
| Active ingredient | 9% |
| No. 1 Moulding plaster | 8% |
| Carbowax 8000 | 13% |
| USG Hydrocal C-base plaster | 69% |
| Magnesium stearate added post granulation | 1% |
| Total | 100% |

Example 21

A dual release tablet, which may be used for potable water, is prepared as follows in Table 49. The pre-mixed powder is dry granulated using heat (60-63° C.) and mixing to improve flowability to the tablet press. The granules are screened to a particle size range of −20+40 mesh. The formulation is as follows:

TABLE 49

Formulation

| Ingredient | Approximate Weight % |
|---|---|
| Active ingredient | 10% |
| DCP | 1% |
| Carbowax 8000 | 10% |
| USG Hydrocal C-base plaster | 78% |
| Magnesium stearate added post granulation | 1% |
| Total | 100% |

Example 22

A dual release tablet that may be used for potable water as described in one of the previous examples is placed into a 200 liter water container. The tablet is expected to control mosquito larvae. One tablet is used per 200 liters of water. Multiple tablets are used when water volume exceeds 200 liters at a rate equivalent to 1 additional tablet for each 200 liter volume increase. A new tablet is used every 60 days or as needed. More frequent treatments are made if monitoring indicates that larval populations have reestablished, or water consumption has rendered initial treatments ineffective. The tablet is also applied as a spot treatment to areas where mosquitoes are breeding at rates appropriate to site size (water volume).

Example 23

A 30 day, 60 day, or 150 day tablet as described in one of the previous examples is used to control mosquito and midge larvae. The tablet is expected to provide up to 30 days, 60 days, or 150 days of residual control. The tablet is applied prior to flooding, on snow and ice in breeding sites prior to spring thaw, or at any time after flooding in listed sites. The treatment is continued through the last brood of the season. The 150 day tablet may last through the entire mosquito season or up to 180 or 170 days, whichever is shorter. The tablet is unaffected in dry down situations and begins working again during subsequent wetting events.

For mosquito control in non- (or low-) flow, shallow depressions (up to 2 feet in depth), the depression is treated on the basis of surface area by placing 1 tablet per 100 square feet. The tablet is placed in the lowest areas of mosquito breeding sites to maintain continuous control as the site alternately floods and dries up.

Storm water drainage areas, sewers and catch basins are treated by placing 1 tablet into each catch basin. For application sites connected by a water system, i.e., storm drains or catch basins, all of the water holding sites in the system are treated to maximize the efficiency of the treatment program.

For application to small contained sites which may not be amenable to a rate of a single tablet per 100 square feet, 1 tablet per contained site (e.g., cesspools and septic tanks, transformer vaults, abandoned pools, and other small artificial water-holding containers) is used.

Example 24

An MHT-100 Portable Hardness Tester manufactured by the Pharma Alliance Group (Valencia, Calif.) was used to measure the hardness of a 6 gram, 25 mm diameter tablet according to one of the formulations presented above. The average hardness of this tablet was determined to be 439.6 Newtons. The tablet was found to be very strong when compared to conventional tablets and products manufactured by, for example, a molded plaster slurry process.

We claim:

1. A dual-release compressed tablet comprising:
a cap composition in an upper layer comprising at least one active agent and a plaster;
a base composition in a lower layer comprising at least one active agent present in an amount of about 0.01-50%, polyethylene glycol present in an amount of about 5-50% and a plaster present in an amount of about 40-90%;
wherein the cap composition in the compressed tablet provides a quick release of the active agent over a period of less than 10 minutes and the base composition in the compressed tablet provides an extended release of the active agent over a period of at least 30 days when placed in water.

2. A method of controlling or eliminating pests at an application site, the method comprising applying the composition of claim 1 to the application site.

3. The method of claim 2, wherein the dual-release tablet is placed in water to dissolve the polyethylene glycol and to hydrolyze the plaster into gypsum to form a gypsum matrix incorporated with the active agent; and
wherein the gypsum matrix provides extended release of the active agent over a period of at least 30 days when placed in water.

4. The method of claim 2, wherein the pests comprise mosquitoes.

5. The tablet of claim 1, wherein the active agent comprises at least one of a pesticide, insecticide, herbicide, fungicide, nematicide, acaricide, bactericide, rodenticide, miticide, algicide, germicide, repellant, and nutrient.

6. The tablet of claim 1, wherein the base composition further comprises at least one additional component selected from a water-soluble binder, a non-water-soluble binder, and a lubricant; and wherein the cap composition further comprises at least one additional component selected from a disintegrating agent, a water-soluble binder, and a non-water-soluble binder.

7. The tablet of claim 6, wherein the cap composition comprises a disintegrating agent comprising an effervescent.

8. The tablet of claim 1, wherein the base composition comprises Plaster of Paris and wherein the cap composition comprises dicalcium phosphate dihydrate, and at least one of citric acid and sodium bicarbonate or a combination thereof.

9. The tablet of claim 6, wherein the active agent is present in the cap composition in an amount of about 0.01-30% wt, the disintegrating agent is present in the cap composition in an amount of about 20-80% wt, and the non-water-soluble binder is present in the cap composition in an amount of about 2-40% wt.

10. The tablet of claim 6, wherein the active agent is present in the cap composition in an amount of about 0.5-10% wt, the plaster is present in the cap composition in an amount of about 10-20% wt, the disintegrating agent is present in the cap composition in an amount of about 20-75% wt, and the non-water-soluble binder is present in the cap composition in an amount of about 2-15% wt.

11. The tablet of claim 10, wherein the active agent is present in the base composition in an amount of about 0.5-12% wt, the plaster is present in the base composition in an amount of about 60-85% wt, and the polyethylene glycol is present in the base composition in an amount of about 8-20% wt.

12. The tablet of claim 1, wherein the active agent is present in the base composition in an amount of about 0.5-12% wt, the plaster is present in the base composition in an amount of about 60-85% wt, and the polyethylene glycol is present in the base composition in an amount of about 8-20% wt.

13. The tablet of claim 1, wherein base composition provides an extended release of the active agent over a period of at least 60 days when placed in water.

14. The tablet of claim 1, wherein the polyethylene glycol is in solid form and has a molecular weight from about 1000 to about 8500.

15. The tablet of claim 1, wherein the active agent comprises spinosad and the plaster comprises plaster of Paris.

16. A compressed tablet comprising a plaster present in an amount of about 40-90% wt, polyethylene glycol present in an amount of about 5-50% wt and at least one active agent present in an amount of about 0.01-50% wt and selected from the group consisting of a pesticide, insecticide, herbicide, fungicide, nematicide, acaricide, bactericide, rodenticide, miticide, algicide, germicide, repellant, and nutrient, wherein the compressed tablet has a hardness of at least about 200

Newtons, wherein the tablet provides an extended release of the active agent over a period of at least 30 days when placed in water.

17. The tablet of claim 16, wherein the tablet has a hardness of at least about 300 Newtons.

18. The tablet of claim 16, wherein the plaster comprises plaster of Paris.

19. The tablet of claim 16, wherein the tablet provides an extended release of the active agent over a period of at least 60 days when placed in water.

20. The tablet of claim 16, wherein the tablet provides an extended release of the active agent over a period of at least 150 days when placed in water.

21. The tablet of claim 16, wherein the plaster comprises plaster of Paris and the active agent comprises spinosad.

22. A method of controlling or eliminating pests at an application site, the method comprising applying the tablet of claim 16 to the application site.

23. The tablet of claim 16, wherein the active agent is present in an amount of about 5-10% wt, the plaster is present in an amount of about 60-85% wt, and the polyethylene glycol is present in an amount of about 5-30% wt.

24. The tablet of claim 23, wherein the tablet further comprises 0.1%-1% wt magnesium stearate.

\* \* \* \* \*